(12) United States Patent
Katrana

(10) Patent No.: US 9,615,930 B2
(45) Date of Patent: Apr. 11, 2017

(54) VARIABLE ANGLE REVERSE HUMERAL TRAY

(71) Applicant: Biomet Manufacturing, LLC, Warsaw, IN (US)

(72) Inventor: Nicholas Katrana, Fort Wayne, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 142 days.

(21) Appl. No.: 14/338,473

(22) Filed: Jul. 23, 2014

(65) Prior Publication Data

US 2014/0379088 A1 Dec. 25, 2014

Related U.S. Application Data

(63) Continuation of application No. 13/464,429, filed on May 4, 2012, now Pat. No. 8,814,941.

(51) Int. Cl.
*A61F 2/40* (2006.01)
*A61F 2/30* (2006.01)

(52) U.S. Cl.
CPC .......... *A61F 2/4081* (2013.01); *A61F 2/4014* (2013.01); *A61F 2/4059* (2013.01); *A61F 2002/30112* (2013.01); *A61F 2002/30332* (2013.01); *A61F 2002/30378* (2013.01); *A61F 2002/30495* (2013.01); *A61F 2002/30507* (2013.01); *A61F 2002/30512* (2013.01); *A61F 2002/30538* (2013.01); *A61F 2002/30604* (2013.01); *A61F 2002/30616* (2013.01); *A61F 2002/30772* (2013.01); *A61F 2002/30774* (2013.01); *A61F 2002/4018* (2013.01); *A61F 2002/4022* (2013.01); *A61F 2002/4029* (2013.01); *A61F 2002/4044* (2013.01)

(58) Field of Classification Search
CPC ................ A61F 2002/4018–2002/4025; A61F 2002/4029–2002/4055; A61F 2002/30538; A61F 2/4607; A61F 2/4014; A61F 2/4059; A61F 2/4081
See application file for complete search history.

(56) References Cited

PUBLICATIONS

Int'l. Prelim. Report on Patentability and Written Opinion of the International Searching Authority for PCT Application No. PCT/US2012/055178, Nov. 13, 2014 (8 pages).
"European Application Serial No. 12767164.2, Decision to grant mailed Feb. 25, 2016", 2 pgs.

*Primary Examiner* — Christopher D Prone
(74) *Attorney, Agent, or Firm* — Schwegman Lundberg & Woessner, P.A.

(57) ABSTRACT

A partial reverse shoulder prosthesis includes a humeral stem and a variable angle tray including a plate including a through hole including at least two cutouts oriented horizontally across from one another, and a repositionable variable angle stem occupying at least a portion of an internal cavity defined by the through hole and including a first washer including threads at least partially defining a first opening, a post at least partially occupying the internal cavity, and a pin insertable into the first opening and having a threaded head sized to engage the threads of at least one of the first washer and the post; wherein the wall of the internal cavity is sized to retain the first washer and at least a portion of the post.

20 Claims, 6 Drawing Sheets

VARIABLE ANGLE REVERSE HUMERAL TRAY

CROSS-REFERENCE TO RELATED APPLICATIONS

This application is a continuation of U.S. patent application Ser. No. 13/464,429 filed May 4, 2012, issued as U.S. Pat. No. 8,814,941 on Aug. 26, 2014, and entitled "Variable Angle Reverse Humeral Tray," the disclosure of which is expressly incorporated in its entirety herein by this reference.

TECHNICAL FIELD

The present disclosure relates to retention devices for surgical procedures and, more specifically, relates to variable angle prosthetic components including reverse shoulder prostheses.

SUMMARY OF THE INVENTION

In accordance with one embodiment of the present disclosure, a partial reverse shoulder prosthesis is provided and comprises a humeral stem and a variable angle tray adapted to be coupled to the humeral stem. The variable angle tray comprises a plate including a through hole at least partially defined by a wall that at least partially defines an internal cavity, the through hole including at least two cutouts oriented horizontally across from one another, and a variable angle stem occupying at least a portion of the internal cavity, the variable angle stem being selectively axially repostionable with respect to the plate to change the axial position of the variable angle stem with respect to the plate. The variable angle stem comprises a first washer including threads at least partially defining a first opening and being insertable into the internal cavity, a post at least partially occupying the internal cavity, the post including a tapered crown and an appendage axially extending from the plate, where the appendage is sized to be received by the humeral stem via a friction fit, and a pin including a threaded head and a longitudinal shaft extending from the threaded head, the pin being insertable into the first opening, where the threaded head is sized to engage the threads of at least one of the first washer and the post. In accordance with this specific embodiment, the wall is sized to retain the first washer and at least a portion of the post within the through hole.

In accordance with another embodiment of the present disclosure, a partial reverse shoulder prosthesis comprises a humeral stem and a variable angle tray adapted to be coupled to the humeral stem. The variable angle tray comprises a plate including a through hole at least partially defined by a wall that at least partially defines an internal cavity, the through hole including at least two cutouts oriented horizontally across from one another, and a variable angle stem occupying at least a portion of the internal cavity, the variable angle stem being selectively axially repositionable with respect to the plate to change an axial position of the variable angle stem with respect to the plate, the variable angle stem comprising a first washer including threads at least partially defining a first opening and being insertable into the internal cavity, a second washer defining a second opening and being insertable into the through hole, the second washer including a widthwise dimension substantially greater than a thickness of the second washer, a post at least partially occupying the internal cavity, the post including threads, a tapered crown and an appendage axially extending from the plate, where the appendage is sized to be received by the humeral stem via a friction fit, and a pin including a threaded head and a longitudinal shaft extending from the threaded head, the pin being insertable into the first opening, where the threaded head is sized to engage the threads of at least one of the first washer and the post. In accordance with this embodiment, the wall is sized to retain the first washer and at least a portion of the post within the through hole.

In accordance with yet another embodiment of the present disclosure, a partial reverse shoulder prosthesis comprises a humeral stem and a variable angle tray adapted to be coupled to the humeral stem, the variable angle tray comprising a plate including a through hole at least partially defined by a wall that at least partially defines an internal cavity, the through hole including at least two cutouts oriented horizontally across from one another, and a variable angle stem occupying at least a portion of the internal cavity, the variable angle stem being selectively axially repositionable with respect to the plate to change an axial position of the variable angle stem with respect to the plate. The variable angle stem comprises a first washer including threads at least partially defining a first opening and being insertable into the internal cavity, a post at least partially occupying the internal cavity, the post including threads, a tapered crown and an appendage axially extending from the plate, where the appendage is sized to be received by the humeral stem via a friction fit, and a pin including a threaded head and a longitudinal shaft extending from the threaded head, the pin being insertable into the first opening, where the threaded head is sized to engage the threads of at least one of the first washer and the post. The wall is sized to retain the first washer and at least a portion of the post within the through hole, and the post includes a hollow adapted to receive at least a portion of the longitudinal shaft of the pin.

In accordance with still another embodiment of the present disclosure, a partial reverse shoulder prosthesis comprises a humeral stem, a humeral cup, and a variable angle tray adapted to be coupled to the humeral stem and the humeral cup, the variable angle tray comprising a plate including an arcuate wall at least partially defining an internal cavity, the through hole including at least two cutouts oriented horizontally across from one another, a bearing adapted to occupy at least a portion of the internal cavity, the bearing being axially and rotationally repositionable with respect to the plate, the bearing operative to selectively expand in at least one dimension to wedge the bearing against the arcuate wall to inhibit axial and rotational repositioning of the bearing with respect to the plate, and a projection adapted to be coupled to the humeral stem in order to mount the variable angle tray to the humeral stem. The arcuate wall is sized to retain a portion of the bearing within the internal cavity, and the bearing comprises a plurality of washers and a threaded fastener.

Still other objects and benefits of the invention will become apparent from the following written description along with the accompanying figures.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein.

Figure 1:
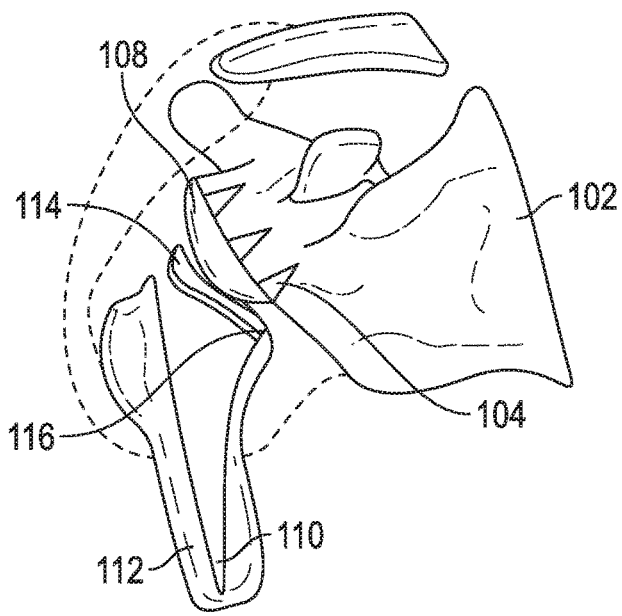
FIG. 1 is a frontal representation of bones, overlaid by skin, of a human shoulder region subsequent to a shoulder replacement where a reverse shoulder prosthesis has been implanted.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Unless defined otherwise, all technical and scientific terms used herein have the same meaning as commonly understood by one of ordinary skill in the art to which this invention belongs. Although any method and materials similar or equivalent to those described herein can be used in the practice or testing of the present invention, the specific methods and materials are now described. Moreover, the techniques employed or contemplated herein are standard methodologies well known to one of ordinary skill in the art and the materials, methods and examples are illustrative only and not intended to be limiting.

The exemplary embodiments of the present disclosure are described and illustrated below to encompass retention devices for surgical procedures and methods of fabricating the retention devices and using the retention devices in a surgical procedure. Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 2:
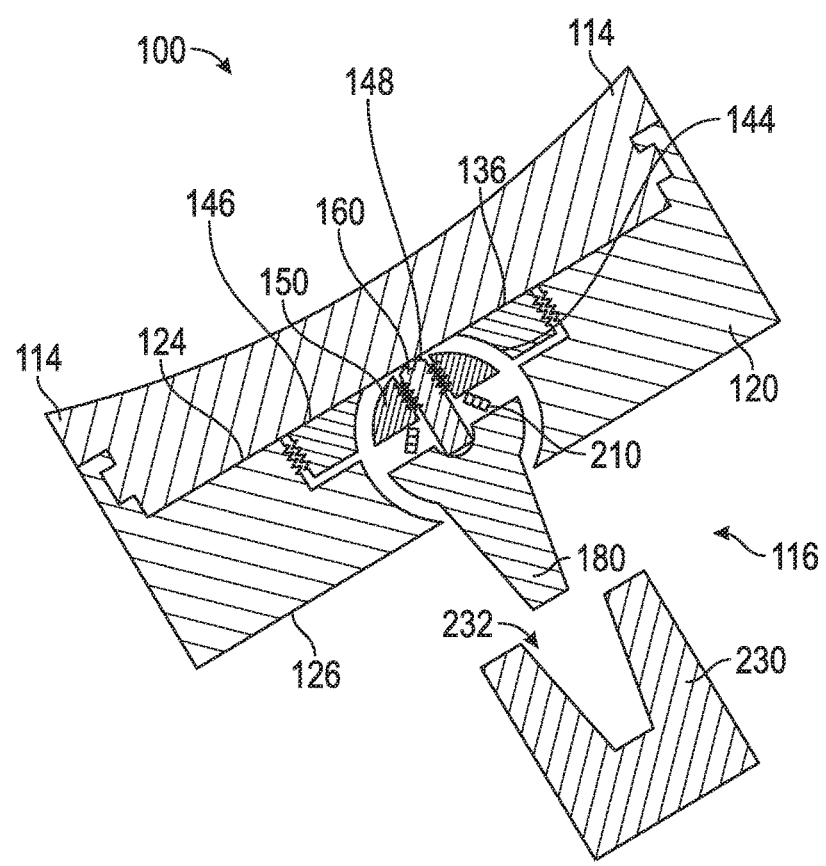
FIG. 2 is a cross-sectional view of a first exemplary partial shoulder joint implant.

Referencing FIGS. 1 and 2, a first exemplary partial shoulder joint implant 100 comprises a portion of a reversible ball and socket joint. The ball portion of the joint is adapted to be coupled to a scapula 102, and includes a scapula retainer 104 and a scapula ball 108. In contrast, the socket portion of the joint comprises a humeral shaft 110 seated within an intramedullary canal of a proximal humerus 112 having a humeral cup 114 mounted to a variable angle tray 116 that is coupled to the humeral shaft.

Figure 3:
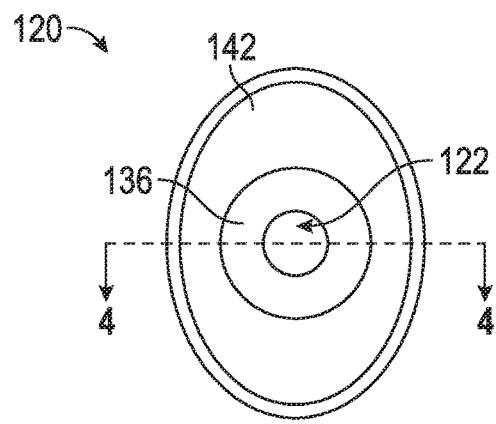
FIG. 3 is a top view of the exemplary plate shown in FIG. 2.
Figure 4:
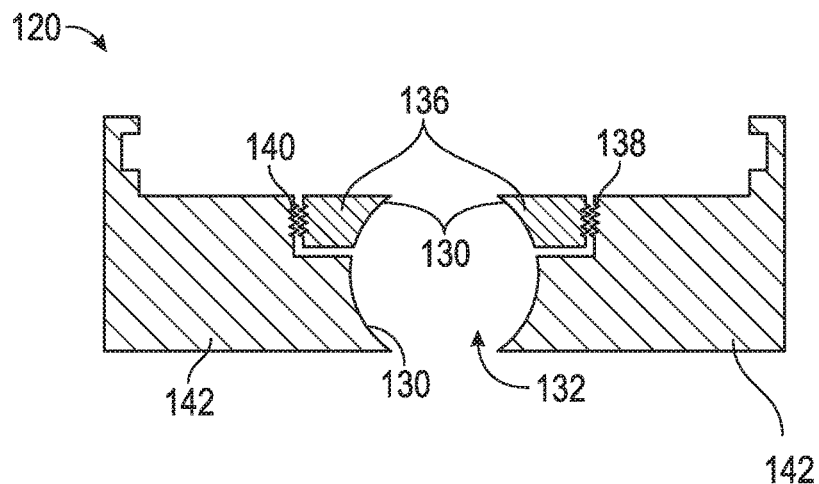
FIG. 4 is a cross-sectional view taken along lines 3-3 of FIG. 3.
Figure 5:
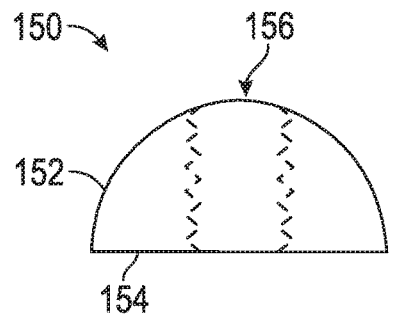
FIG. 5 is a profile view of the exemplary washer of FIG. 2.
Figure 6:
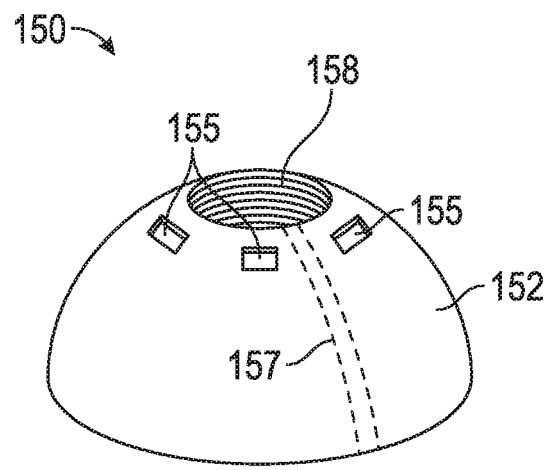
FIG. 6 is an elevated perspective view of the exemplary washer of FIG. 5.
Figure 7:
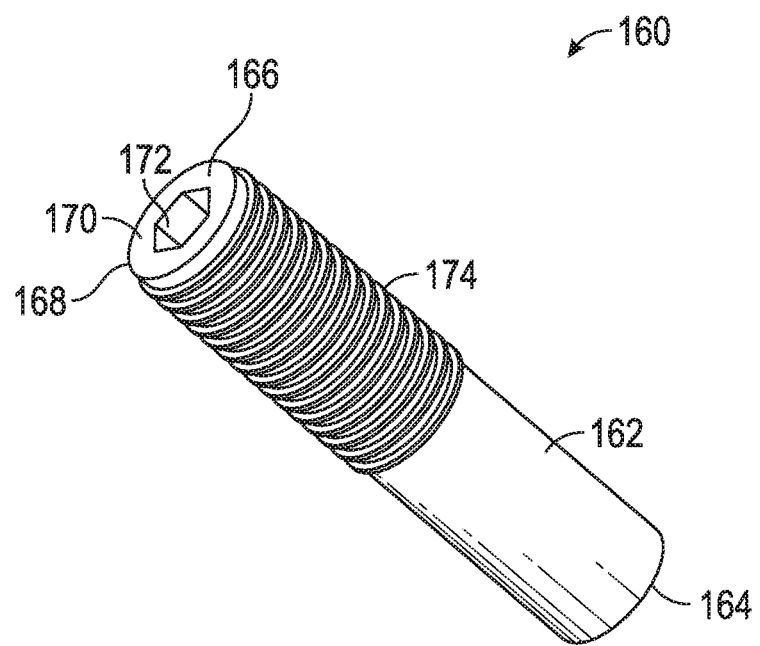
FIG. 7 is an elevated perspective view of the exemplary pin of FIG. 2.

As shown in FIGS. 3 and 4, the variable angle tray 116 includes a plate 120 having an oblong vertical profile. Generally centered within the plate 120 is a through orifice 122 extending between top and bottom surfaces 124, 126. The vertical cross-section of the through orifice 122 is not constant, but rather changes along an axis extending vertically through the orifice. More specifically, an inner circumferential wall 130 of the plate 120 partially defines a spherical cavity 132 where the diameter of the through orifice 122 is at a minimum at the top and bottom surfaces 124, 126, but is at a maximum at the vertical midpoint of the through orifice. In this first exemplary plate 120, the spherical cavity is partially defined by a removable cap 136 that includes threads 138 that engage corresponding threads 140 of a primary portion 142 of the plate. In this fashion, the cap 136 may be disengaged from the primary portion 142 in order to allow components to be seated within the spherical cavity 132 and thereafter reattached to the primary portion to inhibit certain components from egressing from the spherical cavity. The underside of the cap 136 includes an inner circumferential wall 144 that partially defines the spherical cavity 132. The diameter of the inner circumferential wall 144 increases from the underside of the cap 136 to the top planar surface 146 of the cap having an opening 148 formed therein to accept the pin 160.

Alternatively, the cap 136 need not threadably engage the primary portion 142 of the plate 120. Instead, the threaded cap 136 may be secured to the primary portion 142 by using a snap ring or a taper (not shown) received within a corresponding cavity of the primary portion.

Referencing FIGS. 2-6, a washer 150 is adapted to be seated within the spherical cavity 132. This washer 150 comprises a Belleville washer having a convex, rounded exterior surface 152 (that may be smooth or textured) that converges and meets a substantially planar exterior surface 154. The rounded exterior surface 152 may include one or more depressions 155 that circumscribe an orifice 156 extending linearly through the rounded exterior surface 152 at its apex. As will be discussed in more detail hereafter, the one or more of the depressions 155 are adapted to receive projections from a driver 260 that may be used to retain the relative orientation of the washer. The through orifice 156 is substantially perpendicular to the planar exterior surface 154 and is delineated by a circumferential, circular wall having a series of threads 158 adapted to be engaged by a pin 160.

While the washer 150 is shown in exemplary form as a continuous washer, it is also within the scope of the disclosure for the washer to include a radial cut 157 (shown in phantom) that renders the washer discontinuous. In this manner, the circumferential dimension of the washer 150 can more readily expand and contract depending upon the presence or absence of the pin 160. Moreover, while the washer is shown in exemplary form as a Belleville washer, it should also be known that one may use a helical washer, a wave spring washer, or a helical coil in place of the spring washer.

Referring to FIGS. 2-7, the pin 160 comprises a cylindrical shaft 162 having a convex, semispherical distal end 164. Opposite the distal end 164 is a proximal end 166 including a substantially planar surface 168 that circumscribes an opening extending into the interior of the proximal end to create a proximal cavity 170. In exemplary form, this proximal cavity 170 is delineated by a series of vertical walls 172 having a hexagonal configuration. An outer circumference of the proximal end 164 includes a series of threads 174 sized to engage the threads of the 158 of the washer 150. In this manner, the pin 160 may extend into the orifice 156 of the washer 150 and be vertically repositioned therein by rotating the pin with respect to the washer. In addition to engaging the washer 150, the pin 160 is also adapted to engage a post 180.

Figure 8:
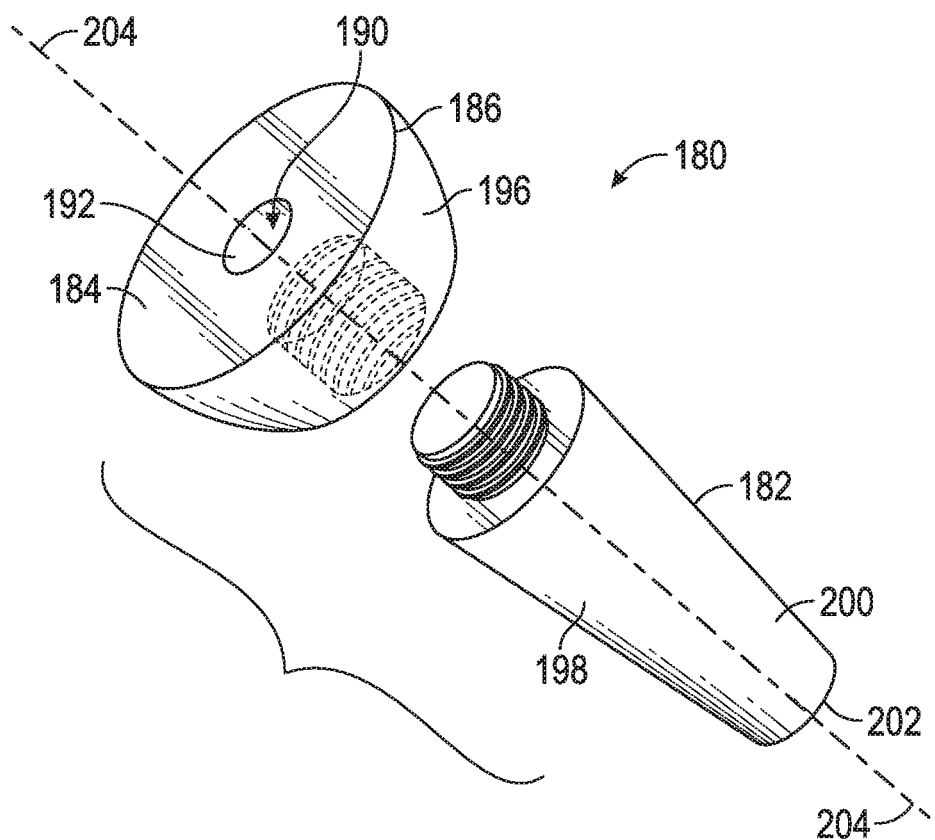
FIG. 8 is an elevated perspective view of the exemplary post of FIG. 2.

Referencing FIG. 8, the post 180 comprises an elongated stem 182 with a generally circular axial cross-section that tapers from proximal to distal. A proximal end 184 of the post 180 includes a generally planar top surface with a circular edge 186 defining the circumferential boundary of the adapter. Inset and centered with respect to the circular edge 186 is a depression 190 formed into the interior of the post 180. In exemplary form, the depression is bounded by a semispherical wall 192 having a diameter that is large enough to accommodate a portion of the proximal end 164 of the pin 160. More specifically, in this exemplary embodiment, the diameter of the semispherical wall 192 is one and a half times the diameter of the pin 160.

Extending proximally from the circular edge 186, a peripheral surface 196 of the post 180 embodies the curvature of a partial sphere and tapers from proximal to distal until reaching a conical surface 198 that circumscribes a frustoconical projection 200 having a substantially planar distal surface 202. In exemplary form, the horizontal cross-section of the frustoconical projection 200 is circular, the diameter of which decreases from proximal to distal between the endpoint of the peripheral surface 196 and the circular perimeter of the planar distal surface 202. In this manner, the frustoconical projection 200 is centered along a longitudinal axis 204 that vertically extends through the depression 190.

Figure 9:
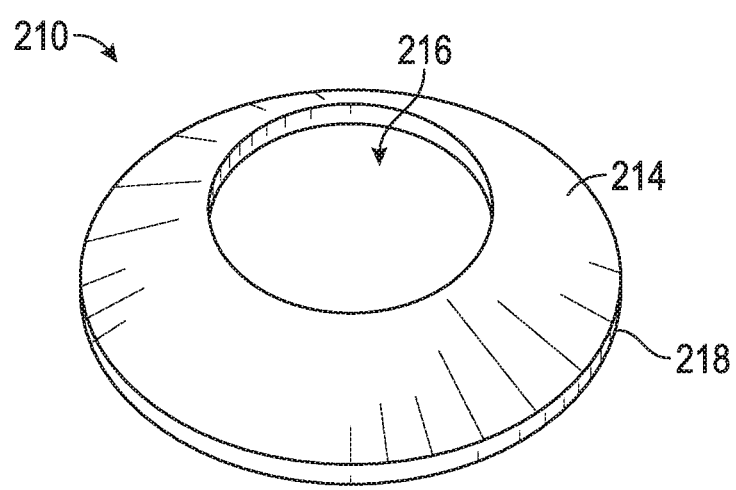
FIG. 9 is an elevated perspective view of the exemplary spring washer of FIG. 2.

Referencing FIG. 9, a spring washer 210 is adapted to interpose the first washer 150 and the post 180 when positioned within the spherical cavity 132. The function of the spring washer 210 is to force the rounded exterior surface 152 of the first washer 150 and the peripheral surface 196 of the post 180 against the inner circumferential walls 130, 144 of the plate 120 and cap 136. The force of the spring washer is chosen to allow axial and rotational repositioning of the assembly (post 180 and washers 150, 210), but provide sufficient resistance to rotational motion of the first washer 150 so that this washer substantially stays in a fixed position when the pin 160 is inserted into the orifice 156 and rotated so the threads 158, 174 engage one another and the pin vertically advances with respect to the first washer.

In this exemplary embodiment, a domed spring washer 210 is utilized. This spring washer 210 includes a convex top surface 214 and a concave bottom surface that are generally parallel to one another and are spaced apart by a thickness dimension. An orifice 216 is axially centered and extends through the spring washer 210. In this exemplary embodiment, the orifice is generally circular. But it should be noted that other shaped orifices could be alternatively used. The outer periphery 218 of the spring washer 210 takes on a circular shape so that the washer has a constant radial distance between the outer periphery and the boundary defining the orifice 216 along the entire circumference, to provide a ring shape. In this exemplary embodiment, the spring washer 210 is fabricated from a metal that includes material properties providing partial elasticity that allows the washer to be compressed (from top and bottom) and spring back into shape when not compressed.

Figure 11:
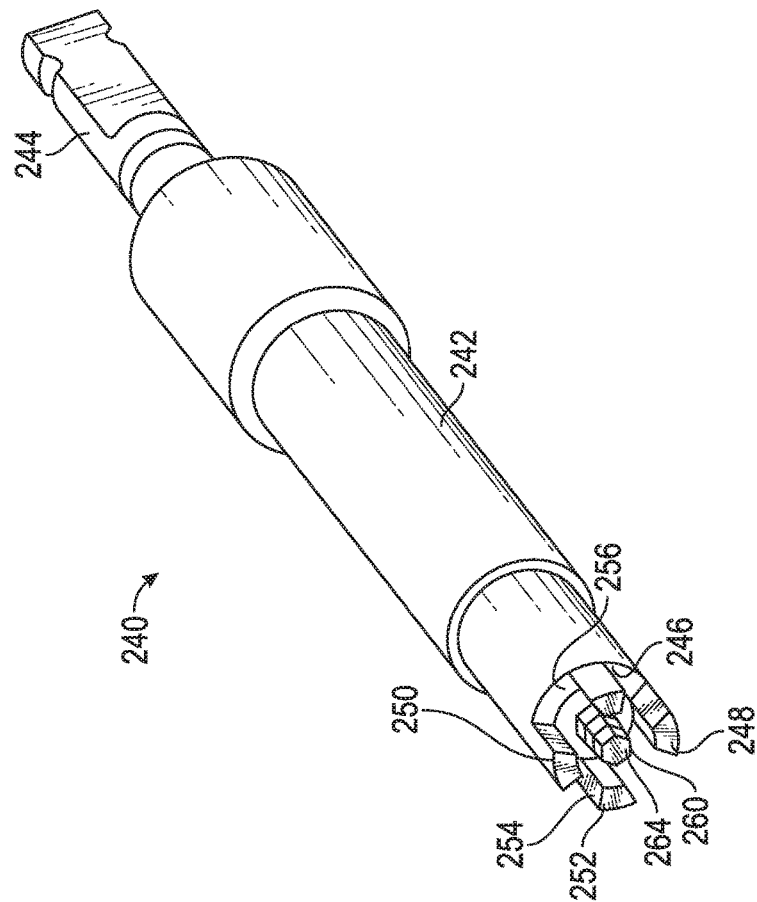
FIG. 11 is an elevated perspective view of a distal end of the exemplary tool of FIG. 10.
Figure 10:
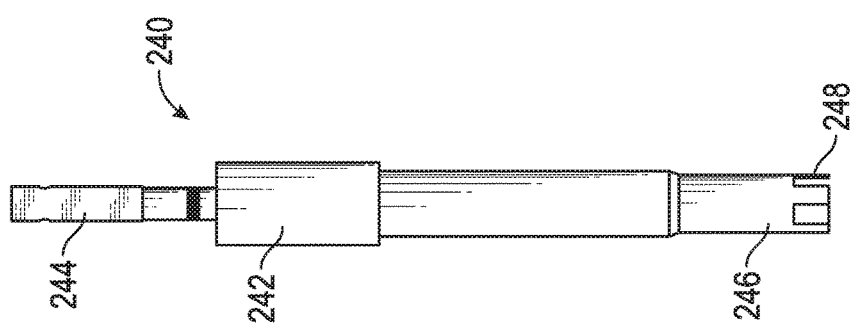
FIG. 10 is a profile view of an exemplary tool for use with the exemplary partial shoulder joint implant of FIG. 2.

Referring to FIGS. 10 and 11, an exemplary tool 240 for use with the partial shoulder joint implant 100 includes an outer housing 242 defining a cylindrical bore occupied by an inner shaft 244 that is longitudinally and rotatably repositionable with respect to the outer housing. The distal end 246 of the outer housing 242 includes four projections 248 evenly spaced and oriented in a circular pattern. In this exemplary embodiment, each projection 248 includes an outer arcuate surface 250 spaced apart from an inner arcuate surface 252 by two planar side surfaces 254 and a bottom surface 256. As will be discussed in more detail below, the projections 248 are adapted to be received within the recesses 155 of the washer 150 in order to inhibit rotation of the washer with respect to the inner shaft 244. At a distal end of the inner shaft 244 is a hexagonal driver 260 having six vertical sidewalls and a substantially planar bottom surface 264. Again, as will be discussed in more detail below, the driver 260 is adapted to be received within the proximal cavity 170 of the pin 160 in order to rotate of the pin with respect to the outer housing 242 and the washer 150.

Referring to FIGS. 1-9, assembly of the partial shoulder joint implant 100 includes seating the humeral shaft 110 within the intramedullary canal of the proximal humerus 112. To ensure the shaft 110 maintains its position with respect to the humerus 112, the shaft 110 may incorporate bone ingrowth materials or features in addition to the use of adhesives or cements interposing the shaft and humerus. This shaft 110 may include a socket adapted to directly receive a portion of the elongated stem 182 of the post 180 via a friction fit, thereby inhibiting relative movement between the post 180 and shaft 110. Conversely, the shaft 110 may include a socket adapted to directly receive a stem adapter 230, which itself includes a cavity 232 for receiving a portion of the elongated stem 182 of the post 180. Relative movement between the stem adapter 230 and the humeral shaft 110 is inhibited after the adapter and shaft are secured via a friction fit. Alternatively, or in addition, the stem adapter 230 may be mounted to the humeral shaft 110 using an adhesive or cement. For purposes of explanation, the assembly will be discussed to include a stem adapter 230.

After the shaft 110 is mounted to the humerus 112 and the stem adapter 230 is mounted to the shaft 110, the variable angle tray 116 may be mounted to the stem adapter. Prior to mounting the variable angle tray 116 to the stem adapter 230, at least a portion of the tray must be assembled. Assembly of the tray 116 begins with the plate 120 without the humeral cup 114 or the removable cap 136 being mounted thereto and without any components being seated within the spherical cavity 132. Thereafter, the post 180 is inserted into the orifice 122 so that a portion of the elongated stem extends beyond the bottom surface 126 of the plate 120. Generally, the peripheral surface 196 of the post 180 will contact the inner circumferential wall 130. Given that the diameter of the orifice 122 is greater than the diameter of the elongated stem 182, but less than the diameter of the proximal end 184 of the post 180, the post is able to be rotationally and axially repositioned with respect to the tray 120.

After the post 180 is inserted into the tray 120, the spring washer 210 is inserted into the spherical cavity 132 so that the orifice 216 is axially aligned with the depression 190 of the post 180. Thereafter, the washer 150 is inserted into the spherical cavity 132 so its orifice 156 is axially aligned with the orifice 216 of the spring washer 210 and the depression 190 of the post 180. At this point, after the washer 150, spring washer 210 and post 180 have been inserted into the spherical cavity 132, the cap 136 is mounted to the plate 120 via a threaded connection between the threads 138 of the cap and threads 140 of the plate. The cap 136 is rotated with respect to the plate 120 until the cap can no longer be rotated, thereby securing the cap to the plate via a friction fit. At this time, the washer 150, spring washer 210 and the post 180 cannot be removed from the spherical cavity 132. But the compilation of the washer 150, spring washer 210 and the post 180 are rotationally and axially repositionable within the spherical cavity 132 at this point.

In order to lock the position of the washer 150, spring washer 210 and the post 180 within the spherical cavity 132, the pin 160 is inserted (distal end 164 first) through the opening 148 of the cap 136, through the orifice 156 of the washer, and through the orifice 216 of the spring washer 210. Eventually, the pin 160 is inserted deep enough that its threads 174 engage the threads 158 of the washer 150. At this point, further penetration of the pin 160 requires the pin to be rotated with respect to the washer 150.

The tool 240 is thereafter used to rotate the pin 160 with respect to the washer 150, as well as axially reposition the washer 150, spring washer 210 and the post 180 with respect to the plate 120. Depending upon the desired angle a surgeon wants to set the tray 116 with respect to the humeral shaft 110, the surgeon manipulates the tool 240 to the desired angle to lock the relative position of the washer 150, spring washer 210 and the post 180 with respect to the plate 120. In exemplary from, the driver 260 is inserted into the proximal cavity 170 of the pin 160 so that rotation of the driver will result in rotation of the pin in the same direction. Likewise, the projections 248 of the outer housing 242 are received within recesses 155 of the washer 150 so that if the outer housing 242 is stationary, so too is the washer. After the tool 240 has engaged the pin 160 and the washer 150, the driver 260 is rotated so the threads 158, 174 engage one another to draw the pin deeper into the spherical cavity 132. At a predetermined point, the distal end 164 of the pin 160 contacts the semicircular wall 192. After this point, continued movement of the pin 160 operates to moves the washer 150 vertically away from the proximal end 184 of the post 180 to eventually form a wedge locking the washer and post in position. This wedge is exhibited when no further rotational motion of the pin 160 with respect to the post 180 is available. When the wedge is created, the axial position of the post 180, and hence its elongated stem 182, is locked in position with respect to the plate 120. At this time, the tool 240 may be removed and the tray 116 mounted to the stem adapter 230. In this manner, relative movement between the stem adapter 230 and the tray 116 is inhibited after the adapter and tray are secured via a friction fit. Alternatively, or in addition, the stem adapter 230 may be mounted to the tray 116 using an adhesive or cement. After the tray 116 is mounted to the stem adapter 230, the humeral cup 114 may be mounted to the tray.

Figure 13:
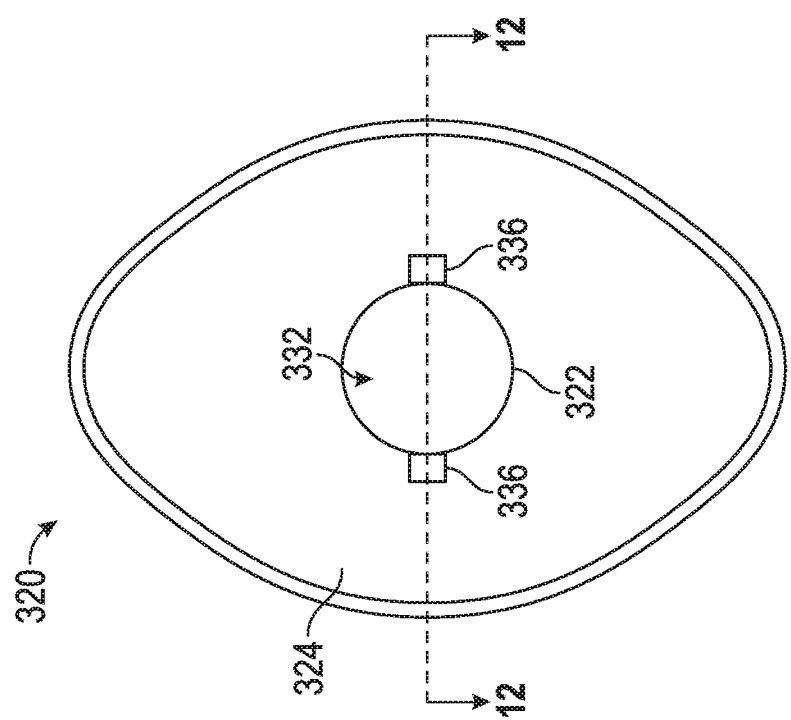
FIG. 13 is a top view of the alternate exemplary plate of FIG. 12.
Figure 12:
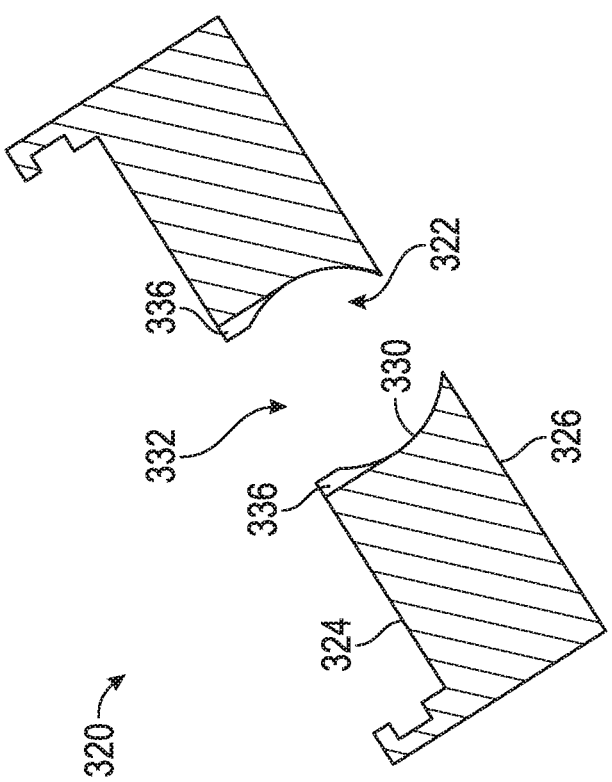
FIG. 12 is a cross-sectional view of an alternate exemplary plate taken along line 13-13 of FIG. 13.

Referring to FIGS. 12 and 13, an alternate exemplary plate 320 may be used in place of the foregoing plate 120. In contrast to the foregoing plate 120, this alternate exemplary plate 320 does not include a removable cap 136. As with the first exemplary plate 120, this alternate exemplary plate 320 includes an oblong vertical profile. Generally centered within the plate 320 is a through orifice 322 extending between top and bottom surfaces 324, 326. The vertical cross-section of the through orifice 322 is not constant, but rather changes along an axis extending vertically through the orifice. More specifically, an inner circumferential wall 330 of the plate 320 partially defines a spherical cavity 332 where the diameter of the through orifice 322 is at a minimum at the top and bottom surfaces 324, 326, but is at a maximum at the vertical midpoint of the through orifice. But the spherical cavity 332 is not entirely spherical. A pair of cutouts 336 are formed vertically through the top surface 324 and radially into the plate 320 to accommodate insertion of washers. The cutouts 336, in exemplary form, may be oriented on the same side of a diametric line and formed vertically to a midpoint of the plate 320. The dimension of the cutouts 336 accommodate vertical insertion of the washers when the washers are turned so that the vertical dimension (i.e., thickness) of the washers is oriented horizontally so the washers can be inserted into the spherical cavity 332 and then axially repositioned so the vertical dimension is oriented vertically. In other words, the thickness of each of the washers is less than the width of the cutouts 336. Because the cutouts 336 do not extend around the entire circumference of the cavity 332, once the washers are inserted into the cavity and axially repositioned, the washers may not be removed from the cavity unless the washers are axially repositioned so that the horizontal position is vertically oriented.

Using the alternate exemplary plate 320 requires using a modified post 180. In this manner, the elongated stem 182 is removable from the proximal end 184 via a threaded connection. More specifically, the elongated stem 182 includes a male threaded connection that is received with a female threaded connection of the proximal end 184. As a result, only the proximal end 184 of the post 180 need to inserted in between the cutouts 336. After the proximal end 184 of the post 180 is within the spherical cavity 332, the elongated stem 182 is coupled to the proximal end by engagement of the threaded connections. Beyond these modifications, all other aspects are substantially the same as the first exemplary embodiment.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

What is claimed is:

1. A partial reverse shoulder prosthesis comprising:
   a humeral stem; and
   a variable angle tray adapted to be coupled to the humeral stem, the variable angle tray comprising:
   a plate including a through hole at least partially defined by a wall that at least partially defines an internal cavity, the through hole including at least two cutouts oriented horizontally across from one another; and
   a variable angle stem occupying at least a portion of the internal cavity, the variable angle stem being selectively axially repositionable with respect to the plate to change the axial position of the variable angle stem with respect to the plate, the variable angle stem comprising:
   a first washer including threads at least partially defining a first opening and being insertable into the internal cavity;
   a post at least partially occupying the internal cavity, the post including a tapered crown and an appendage axially extending from the plate, where the appendage is sized to be received by the humeral stem via a friction fit; and
   a pin including a threaded head and a longitudinal shaft extending from the threaded head, the pin being insertable into the first opening, where the threaded head is sized to engage the threads of at least one of the first washer and the post;
   wherein the wall is sized to retain the first washer and at least a portion of the post within the through hole.

2. The partial reverse shoulder prosthesis of claim 1, wherein the first washer is discontinuous.

3. The partial reverse shoulder prosthesis of claim 1, wherein the at least two cutouts are both oriented on the same side of a horizontal diametric chord of the through hole.

4. The partial reverse shoulder prosthesis of claim 1, wherein at least one of the first washer and the tapered crown includes a rounded circumferential surface adapted to contact the wall.

5. The partial reverse shoulder prosthesis of claim 4, wherein the rounded circumferential surface is at least one of smooth and textured.

6. The partial reverse shoulder prosthesis of claim 1, wherein at least one of the first washer and the tapered crown includes a sloped circumferential surface adapted to contact the wall.

7. The partial reverse shoulder prosthesis of claim 6, wherein the sloped circumferential surface is at least one of smooth and textured.

8. A partial reverse shoulder prosthesis comprising:
   a humeral stem; and
   a variable angle tray adapted to be coupled to the humeral stem, the variable angle tray comprising:
   a plate including a through hole at least partially defined by a wall that at least partially defines an internal cavity, the through hole including at least two cutouts oriented horizontally across from one another; and
   a variable angle stem occupying at least a portion of the internal cavity, the variable angle stem being selectively axially repositionable with respect to the plate to change an axial position of the variable angle stem with respect to the plate, the variable angle stem comprising:
   a first washer including threads at least partially defining a first opening and being insertable into the internal cavity;
   a second washer defining a second opening and being insertable into the through hole, the second washer including a widthwise dimension substantially greater than a thickness of the second washer;
   a post at least partially occupying the internal cavity, the post including threads, a tapered crown and an appendage axially extending from the plate, where the appendage is sized to be received by the humeral stem via a friction fit; and
   a pin including a threaded head and a longitudinal shaft extending from the threaded head, the pin being insertable into the first opening, where the threaded head is sized to engage the threads of at least one of the first washer and the post;
wherein the wall is sized to retain the first washer and at least a portion of the post within the through hole.

9. The partial reverse shoulder prosthesis of claim 8, wherein the at least two cutouts are both oriented on the same side of a horizontal diametric chord of the through hole.

10. The partial reverse shoulder prosthesis of claim 8, wherein the second washer is a spring washer.

11. The partial reverse shoulder prosthesis of claim 8, wherein the second washer comprises a Belleville washer.

12. A partial reverse shoulder prosthesis, comprising:
a humeral stem; and
a variable angle tray adapted to be coupled to the humeral stem, the variable angle tray comprising:
    a plate including a through hole at least partially defined by a wall that at least partially defines an internal cavity, the through hole including at least two cutouts oriented horizontally across from one another; and
    a variable angle stem occupying at least a portion of the internal cavity, the variable angle stem being selectively axially repositionable with respect to the plate to change an axial position of the variable angle stem with respect to the plate, the variable angle stem comprising:
        a first washer including threads at least partially defining a first opening and being insertable into the internal cavity;
        a post at least partially occupying the internal cavity, the post including threads, a tapered crown and an appendage axially extending from the plate, where the appendage is sized to be received by the humeral stem via a friction fit; and
        a pin including a threaded head and a longitudinal shaft extending from the threaded head, the pin being insertable into the first opening, where the threaded head is sized to engage the threads of at least one of the first washer and the post;
wherein the wall is sized to retain the first washer and at least a portion of the post within the through hole; and
wherein the post includes a hollow adapted to receive at least a portion of the longitudinal shaft of the pin.

13. The partial reverse shoulder prosthesis of claim 12, wherein the at least two cutouts are both oriented on the same side of a horizontal diametric chord of the through hole.

14. The partial reverse should prosthesis of claim 12, further comprising a humeral cup mounted to the variable angle tray.

15. A partial reverse shoulder prosthesis comprising:
a humeral stem;
a humeral cup; and
a variable angle tray adapted to be coupled to the humeral stem and the humeral cup, the variable angle tray comprising:
    a plate including an arcuate wall at least partially defining an internal cavity, the through hole including at least two cutouts oriented horizontally across from one another;
    a bearing adapted to occupy at least a portion of the internal cavity, the bearing being axially and rotationally repositionable with respect to the plate, the bearing operative to selectively expand in at least one dimension to wedge the bearing against the arcuate wall to inhibit axial and rotational repositioning of the bearing with respect to the plate; and
    a projection adapted to be coupled to the humeral stem in order to mount the variable angle tray to the humeral stem;
wherein the arcuate wall is sized to retain a portion of the bearing within the internal cavity; and
wherein the bearing comprises a plurality of washers and a threaded fastener.

16. The partial reverse shoulder prosthesis of claim 15, wherein the at least two cutouts are both oriented on the same side of a horizontal diametric chord of the through hole.

17. The partial reverse shoulder prosthesis of claim 15, wherein:
the plate includes a through opening that communicates with the internal cavity; and
the internal cavity is partially spherical shaped.

18. The partial reverse shoulder prosthesis of claim 15, wherein:
the plurality of washers comprise a first washer and a second washer;
the threaded fastener is sized to extend through and engage a threaded hole of the first washer;
the threaded fastener is sized to engage the second washer;
movement of the threaded fastener in a first direction with respect to the first washer causes the bearing to expand and wedge the bearing against the arcuate wall to inhibit axial and rotational repositioning of the bearing with respect to the plate; and
movement of the threaded fastener in a second direction, generally opposite the first direction, with respect to the first washer causes the bearing to contract and allow axial and rotational repositioning of the bearing with respect to the plate.

19. The partial reverse shoulder prosthesis of claim 15, wherein the first washer includes a convex exterior surface adapted to contact the arcuate wall of the plate.

20. A partial reverse shoulder prosthesis system comprising:
a humeral stem;
a variable angle tray adapted to be coupled to the humeral stem, the variable angle tray comprising:
    a plate including a through hole at least partially defined by a wall that at least partially defines an internal cavity, the through hole including at least two cutouts oriented horizontally across from one another; and
    a variable angle stem occupying at least a portion of the internal cavity, the variable angle stem being selectively axially repositionable with respect to the plate to change the axial position of the variable angle stem with respect to the plate, the variable angle stem comprising:
        a first washer including threads at least partially defining a first opening and being insertable into the internal cavity;
        a post at least partially occupying the internal cavity, the post including a tapered crown and an appendage axially extending from the plate, where the appendage is sized to be received by the humeral stem via a friction fit; and
        a pin including a threaded head and a longitudinal shaft extending from the threaded head, the pin being insertable into the first opening, where the threaded head is sized to engage the threads of at least one of the first washer and the post, wherein the wall is sized to retain the first washer and at least a portion of the post within the through hole; and a driver including a first engagement device and a second engagement device, wherein the first engagement device is rotatably repositionable with respect to the second engagement device, wherein the first engagement device engages the pin, and wherein the second engagement device engages the first washer.

* * * * *

UNITED STATES PATENT AND TRADEMARK OFFICE
CERTIFICATE OF CORRECTION

PATENT NO. : 9,615,930 B2
APPLICATION NO. : 14/338473
DATED : April 11, 2017
INVENTOR(S) : Nicholas Katrana It is certified that error appears in the above-identified patent and that said Letters Patent is hereby corrected as shown below:

In the Claims

In Column 10, Line 48, in Claim 8, delete "repostionable" and insert --repositionable-- therefor In Column 11, Line 25, in Claim 12, delete "repostionable" and insert --repositionable-- therefor In Column 12, Line 52, in Claim 20, delete "repostionable" and insert --repositionable-- therefor Signed and Sealed this
Twelfth Day of June, 2018

Andrei Iancu
*Director of the United States Patent and Trademark Office*